(12) United States Patent
Vander Bush et al.

(10) Patent No.: US 7,428,807 B2
(45) Date of Patent: Sep. 30, 2008

(54) METHOD FOR PACKAGING MEDICAL CONTAINERS

(75) Inventors: Edward Vander Bush, Downingtown, PA (US); Robert Nase, Reading, PA (US); Hiroshi Togashi, Sano (JP); Hubert Jansen, Stolberg (DE); John Paproski, North Wales, PA (US)

(73) Assignees: West Pharmaceutical Services, Inc., Lionville, PA (US); Daikyo Seiko Ltd., Tokyo (JP)

( * ) Notice: Subject to any disclaimer, the term of this patent is extended or adjusted under 35 U.S.C. 154(b) by 0 days.

(21) Appl. No.: 11/680,710

(22) Filed: Mar. 1, 2007

(65) Prior Publication Data

US 2007/0157564 A1   Jul. 12, 2007

Related U.S. Application Data

(62) Division of application No. 11/171,814, filed on Jun. 30, 2005.

(60) Provisional application No. 60/584,826, filed on Jul. 1, 2004.

(51) Int. Cl.
*B65B 55/02* (2006.01)
*B65B 31/04* (2006.01)
*B65B 21/24* (2006.01)
*B65B 53/00* (2006.01)

(52) U.S. Cl. .............. 53/425; 53/434; 53/441; 53/445; 53/469; 53/492; 206/432; 206/497; 206/524.8; 422/22; 422/23

(58) Field of Classification Search .................. 53/434, 53/469, 425, 492, 475, 512, 284.7, 167, 474, 53/445, 441, 556, 432, 510, 48.1, 48.2, 433, 53/511; 414/412; 422/22, 23; 206/432, 206/497, 524.8

See application file for complete search history.

(56) References Cited

U.S. PATENT DOCUMENTS 2,629,421 A   2/1953 Ayres
2,658,011 A * 11/1953 Price .................... 134/22.1

(Continued)

FOREIGN PATENT DOCUMENTS

WO   WO 9425366 A1 * 11/1994

OTHER PUBLICATIONS

Daikyo Seiko, Ltd. Company Profile and Catalog, (Feb. 20, 2003).

(Continued)

*Primary Examiner*—Stephen F Gerrity
(74) *Attorney, Agent, or Firm*—Panitch Schwarze Belisario & Nadel LLP (57) ABSTRACT

A vacuum packaging system for transporting a plurality of medical containers including a tray that supports the medical containers and an air impervious flexible film defining an internal cavity. The air impervious flexible film completely surrounds the tray and the medical containers. The internal cavity is evacuated to a predetermined vacuum level below atmospheric pressure. A method for packaging the plurality of medical containers for transportation in the tray includes inserting the medical containers into the tray, inserting the tray filled with medical containers into the internal cavity, evacuating the internal cavity to a predetermined vacuum pressure and sealing the flexible film such that the predetermined vacuum pressure is generally maintained in the internal cavity.

16 Claims, 8 Drawing Sheets

U.S. PATENT DOCUMENTS

| | | | | |
|---|---|---|---|---|
| 2,771,399 | A | * | 11/1956 | Savage ........................ 435/33 |
| 3,562,999 | A | * | 2/1971 | Barbedienne ................ 53/441 |
| 3,643,812 | A | | 2/1972 | Mander et al. |
| 3,677,774 | A | * | 7/1972 | Rausing ...................... 426/108 |
| 3,746,160 | A | * | 7/1973 | Thompson et al. .......... 206/497 |
| 3,850,340 | A | | 11/1974 | Siemonsen et al. |
| 4,365,715 | A | * | 12/1982 | Egli .......................... 206/524.8 |
| 4,457,123 | A | * | 7/1984 | Hoehn ......................... 53/492 |
| 4,523,679 | A | | 6/1985 | Paikoff et al. |
| 4,548,824 | A | | 10/1985 | Mitchell et al. |
| 4,549,656 | A | | 10/1985 | Barnes et al. |
| 4,718,463 | A | * | 1/1988 | Jurgens et al. ................. 141/11 |
| 4,730,730 | A | * | 3/1988 | Clarkson ..................... 206/497 |
| 4,754,595 | A | * | 7/1988 | Sanderson ..................... 53/425 |
| 5,014,494 | A | * | 5/1991 | George ......................... 53/425 |
| 5,035,323 | A | * | 7/1991 | Daniels et al. ............... 206/386 |
| 5,069,594 | A | * | 12/1991 | Bott et al. .................... 414/412 |
| 5,426,922 | A | * | 6/1995 | Bott et al. ..................... 53/567 |
| 5,439,132 | A | | 8/1995 | Gorlich |
| 5,477,663 | A | * | 12/1995 | Smith et al. ................... 53/475 |
| 6,059,111 | A | * | 5/2000 | Davila et al. ................ 206/438 |
| 6,161,695 | A | | 12/2000 | Nicolais |
| 6,189,292 | B1 | * | 2/2001 | Odell et al. .................... 53/425 |
| 6,412,639 | B1 | | 7/2002 | Hickey |
| 6,588,594 | B2 | * | 7/2003 | Andersen et al. ............ 206/497 |
| 6,715,264 | B2 | * | 4/2004 | Liakopoulos et al. ......... 53/434 |
| 2003/0206825 | A1 | * | 11/2003 | Vellutato ...................... 422/22 |
| 2004/0187438 | A1 | * | 9/2004 | Clarke et al. ................... 53/400 |

OTHER PUBLICATIONS

Non-Final Office Action dated Aug. 8, 2007 in U.S. Appl. No. 11/171,814, filed Jun. 30, 2005, Paper No. 20070705.
Non-Final Office Action dated Dec. 29, 2006 in U.S. Appl. No. 11/171,814, filed Jun. 30, 2005, Paper No. 20061130.
Final Office Action dated May 17, 2007 in U.S. Appl. No. 11/171,814, filed Jun. 30, 2005, Paper No. 20070508.
Non-Final Office Action, Restriction Requirement dated Oct. 18, 2006 in U.S. Appl. No. 11/171,814, filed Jun. 30, 2005, Paper No. 20061013.
Response to Non-Final Office Action dated Nov. 16, 2006 in U.S. Appl. No. 11/171,814, filed Jun. 30, 2005.
Response to Non-Final Office Action dated Mar. 28, 2007 in U.S. Appl. No. 11/171,814, filed Jun. 30, 2005.
Response to Final Office Action and an RCE request dated Jul. 20, 2007 in U.S. Appl. No. 11/171,814, filed Jun. 30, 2005.

* cited by examiner

METHOD FOR PACKAGING MEDICAL CONTAINERS

CROSS-REFERENCE TO RELATED APPLICATIONS

This application is a division of pending U.S. patent application Ser. No. 11/171,814, filed Jun. 30, 2005, which claims the benefit of U.S. Provisional Application No. 60/584,826, filed Jul. 1, 2004.

BACKGROUND OF THE INVENTION

Medical containers generally must be sterile, have a low level of non-viable particulate matter and have a low or undetectable pyrogen level prior to the introduction of medication or another medical product into the medical container such that the product is not contaminated. One having ordinary skill in the art will realize that the medical containers are not necessarily completely sterile and free of all pyrogens prior to being filled with a medical product. However, the medical containers may be referred to as being sterile, pyrogen free and non-viable particulate matter free, meaning that the medical containers have a high sterility, a low or non-pyrogenic level and a low level of non-viable particulate matter. Common medical containers, for example, vials and syringes, are typically shipped from the vial or syringe molder in a permeable, non-sterile package and are sterilized, washed and depyrogenated to reduce pyrogen levels before introduction into a vial or syringe filling assembly line.

Glass vials and syringes may be washed and heated to a predetermined temperature for a predetermined time to eliminate non-viable particulate matter, reduce pyrogen levels and sterilize the vials and syringes. This process is relatively simple for a manufacturer who fills vials or syringes to perform because the glass vials and syringes are relatively easy to wash and place into a heated oven for the predetermined time. However, polymeric or plastic vials and syringes are typically unable to withstand the temperature required to reduce pyrogens to a non-pyrogenic level and sterilize the vials and syringes. The plastic vials and syringes may be washed and irradiated to reduce pyrogens and sterilize the vials and syringes, but the plastic vials and syringes are difficult to dry and the process is time consuming and generally will not result in removal of pyrogens to an acceptable level for filling. Accordingly, it would be advantageous to ship plastic vials and syringes directly from the vial and syringe molder that are sterile and pyrogen free during and after their shipment. Shipment of sterilized plastic vials and syringes to the assembly line would eliminate the extra sterilization, pyrogen reduction and non-viable particulate matter reduction processes that must be performed. In addition, vials and syringes are typically sterile, have a low pyrogen level and a low non-viable particulate matter level when they come out of a molding process and it would be advantageous to ship the vials and syringes in this condition without impacting their sterility, low pyrogen level and low non-viable particulate level.

Medical containers are typically shipped in boxes, trays or other like shipping containers that are permeable, not sterile and have a relatively high level of pyrogens. In addition, the shipping containers are often utilized to hold the medical containers in an orderly fashion in a clean room such that a robot is able to pick the medical containers out of the shipping containers and place them onto an assembly line. Accordingly, in order to enter the clean room environment, the shipping containers must also be sterile, have a low non-viable particulate matter level and have a low pyrogen level. Therefore, the shipping containers must also be sterilized, depyrogenated and cleaned of particulate matter before they enter the clean room. It would be advantageous to directly ship sterile, pyrogen free and non-viable particulate matter free medical containers in a sterilized, pyrogen free and non-viable particulate matter free container that may be taken directly to a clean room for filling of the medical containers.

Further, when medical containers are shipped in permeable boxes or trays in permeable bags, the vials and syringes may shift or vibrate during their shipment. When the vials and syringes shift and/or vibrate during transport, they may rub against each other causing surface damage and potentially introducing particulates into the bag and onto the vials and syringes. Accordingly, it would be advantageous to ship the vials and syringes in a package that generally does not permit significant shifting, movement or vibration of the vials and syringes, thereby resulting in reduced damage to the vials and syringes during shipping.

BRIEF SUMMARY OF THE INVENTION

Briefly stated, a preferred embodiment of the present invention is directed to a vacuum packaging system for transporting a plurality of medical containers. The vacuum packaging system includes a tray that supports the medical containers and an air impervious flexible film defining an internal cavity. The air impervious flexible film completely surrounds the tray and the medical containers. The internal cavity is evacuated to a predetermined vacuum level below atmospheric pressure.

In another aspect, a preferred embodiment of the present invention is directed to a method for packaging a plurality of medical containers for transportation in a tray within an evacuated internal cavity of an air impervious flexible film. The method includes the steps of inserting the medical containers into the tray, inserting the tray filled with the medical containers into the internal cavity, evacuating the internal cavity to a predetermined vacuum pressure such that the flexible film surrounds and engages the tray and at least portions of the medical containers and sealing the flexible film such that the predetermined vacuum pressure is generally maintained in the internal cavity.

BRIEF DESCRIPTION OF THE SEVERAL VIEWS OF THE DRAWINGS

The following detailed description of the preferred embodiments of the present invention will be better understood when read in conjunction with the appended drawings. For the purposes of illustrating the invention, there is shown in the drawings embodiments which are presently preferred. It is understood, however, that the invention is not limited to the precise arrangements and instrumentalities shown. In the drawings.

DETAILED DESCRIPTION OF THE INVENTION

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the vacuum package system and designated parts thereof. The terminology includes the words specifically mentioned, derivatives thereof and words of similar import. Additionally, the word "a" as used in the specification means "at least one."

Referring to the drawings in detail, wherein like numerals indicate like elements throughout, there is shown in FIGS. 1-5 and 8 a first preferred embodiment of a vacuum packaging system, generally designated 10, for transporting a plurality of medical containers 16. The vacuum packaging system 10 includes an air impervious film 12, a tray 14 and the plurality of medical containers 16. In the first preferred embodiment, the medical containers 16 are preferably comprised of vials 16 and the air impervious film 12 is preferably comprised of a vacuum bag 12 having an internal cavity 12a. The medical containers 16 are not limited to vials 16 and the air impervious film 12 is not limited to a vacuum bag 12. For example, the medical containers 16 may be comprised of nearly any container or vessel that is transported from a medical container manufacturer to an end user. In addition, the air impervious film 12 may be comprised of a film or sheet of material that is formed into a container or bag having a cavity into which the tray 14 may be inserted. The plurality of vials 16 is preferably stackable in the tray 14 and the vacuum bag 12 is preferably large enough to hold the tray 14 with the plurality of vials 16 stacked therein.

The tray 14 supports the vials 16 in the first preferred embodiment and the air impervious film 12 defines the internal cavity 12a. In an assembled configuration, the air impervious flexible film 12 completely surrounds the tray 14 and the medical containers 16 and the internal cavity 12a is evacuated to a predetermined vacuum level below atmospheric pressure. When the internal cavity 12a is evacuated, the air impervious flexible film 12 is preferably in facing engagement with at least portions of the vials 16 and the tray 14, thereby holding the vials 16 in a relatively fixed position in the tray 14 such that the vials 16 generally do not move during transportation. Specifically, it is preferred that the tray 14 and air impervious film 12 hold the vials 16 in a manner that generally prevents significant movement of the vials 16 such that the vials 16 generally do not rub against each other during shipping, as will be described in greater detail below In the first preferred embodiment, the vials 16 are constructed of a polymeric or, preferably, a plastic material and have a shape of a conventional vial that typically holds medication, another liquid substance, a powdered medical product or another like product. The vials 16 are not limited to plastic constructions and may be constructed of nearly any material that may be formed into the general shape of the vials 16, perform the typical functions of the vials 16 and withstand the normal operating conditions of the vials 16. For example, the vials 16 may be constructed of nearly any polymeric or glass material. However, the plastic material is preferred for construction of the vials 16 because of the ease of moldability of the plastic material and the generally high resistance to breakage if dropped or impacted by an external force. The plastic material also provides surfaces that are receptive to sterilization and pyrogen elimination.

In the first preferred embodiment, the tray 14 is constructed of a thermoformed polymeric material. The tray 14 is not limited to being thermoformed and may be constructed using nearly any manufacturing process that is able to form the general shape and size of the tray 14, such as injection molding, machining or another like manufacturing process. In the preferred embodiment, the tray 14 is constructed of a thermoformed plastic material that has a shape and size that accommodates stacking and storage of the plurality of vials 16. The thermoformed plastic material is preferred because of its formability, ability to be sterilized and relatively low cost. The tray 14 and vacuum bag 12 are also preferably transparent or semi-transparent so that a user is able to perform a visual inspection of the vials 16 stacked in the tray 14 in the assembled configuration or at any time the vials 16 are stacked in the tray 14, but are not so limited. The vacuum bag 12 and tray 14 may also be constructed of a semi-transparent or opaque material.

Referring to FIGS. 1-5, in the first preferred embodiment, the tray 14 includes opposing first and second sidewalls 32a, 32b and opposing front and rear walls 34, 36. In the first preferred embodiment, the tray 14 has a generally square or rectangular-shape with the walls 32a, 32b, 34, 36 separated from each other by a floor 14a. The preferred walls 32a, 32b, 34, 36 extend from the floor 14a to a top edge 14b. In the first preferred embodiment, the tray 14 has a tray height $H_w$ of approximately one and seven-eighths inches (1⅞"). The tray height $H_w$ is not limited to the above-listed height and may have nearly any height that is able to accommodate the containment of nearly any sized and shaped medical container 16. The one and seven-eighths inch tray height $H_w$ for the walls 32a, 32b, 34, 36 is preferred for packaging and transporting the preferred vials 16 in the tray 14.

Referring to FIGS. 1-4, in the first preferred embodiment, side pockets 30 are formed in the first and second sidewalls 32a, 32b. The side pockets 30 are preferably arc-shaped depressions formed in the first and second sidewalls 32a, 32b that extend outwardly relative to a center of the tray 14 and conform to at least a portion of an external surface of one of the medical containers 16 or vials 16 when the vials 16 are located in the tray 14 proximate one of the side pockets 30. In the first preferred embodiment, each of the first and second sidewalls 32a, 32b include six (6) side pockets 30 to accommodate twelve (12) staggered rows of medical containers or vials 16. The side pockets 30 preferably conform to at least a portion of the external surface of the vials 16 to provide stability for each row of vials 16 within the tray 14 to generally prevent the row of vials 16 from toppling or falling over. Side peaks 30a are also defined between each of the side pockets 30 and conform to a relatively smaller portion of the external surface of at least one medical container or vial 16. The peaks 30a in concert with an opposing side pocket 30 formed on an opposite sidewall 32a, 32b provide additional stability for the row of vials 16. The tray 14 is not limited to the inclusion of the arc-shaped side pockets 30 and the peaks 30a that generally conform to a portion of the external surface of the vials 16. For example, the sidewalls 32a, 32b may have a generally planar internal surface or may have a flexible surface that is able to flex to conform to a portion of the external shape of the containers 16. In addition, the tray 14 is not limited to the above-listed number of pockets 30 and peaks 30a on the sidewalls 32a, 32b and may include nearly any number of side pockets 30 and peaks 30a to accommodate nearly any number of containers 16. However, the side pockets 30 and peaks 30a are preferred in the sidewalls 32a, 32b to provide stability for the vials 16 when they are stacked in the tray 14.

In the first preferred embodiment, the tray 14 also includes front pockets 34a in the front wall 34 and rear pockets 36a in the rear wall 36. The front and rear pockets 34a, 36a preferably conform to at least a portion of the external surface of one of the medical containers or vials 16 when the containers 16 are located in the tray 14 proximate one of the front and rear pockets 34a, 36a. In the first preferred embodiment, the front and rear walls, 34, 36 each include twelve opposing front and rear pockets 34a, 36a to accommodate twelve columns of vials 16 in the tray 14. The tray 14 is not limited to the inclusion of twelve front and rear pockets 34a, 36a on the front and rear walls 34, 36 nor to the inclusion of any front and rear pockets 34a, 36a. For example, the tray 14 may include nearly any number of front and rear pockets 34a, 36a that provide stability for the vials 16 when they are mounted or inserted into the tray 14 or may include no front and rear pockets 34a, 36a such that the vials 16 simply rest against a planar front and/or rear wall 34, 36. However, the front and rear pockets 34a, 36a are preferred to provide stability for the vials 16 when they are placed into the tray 14.

Figure 1:
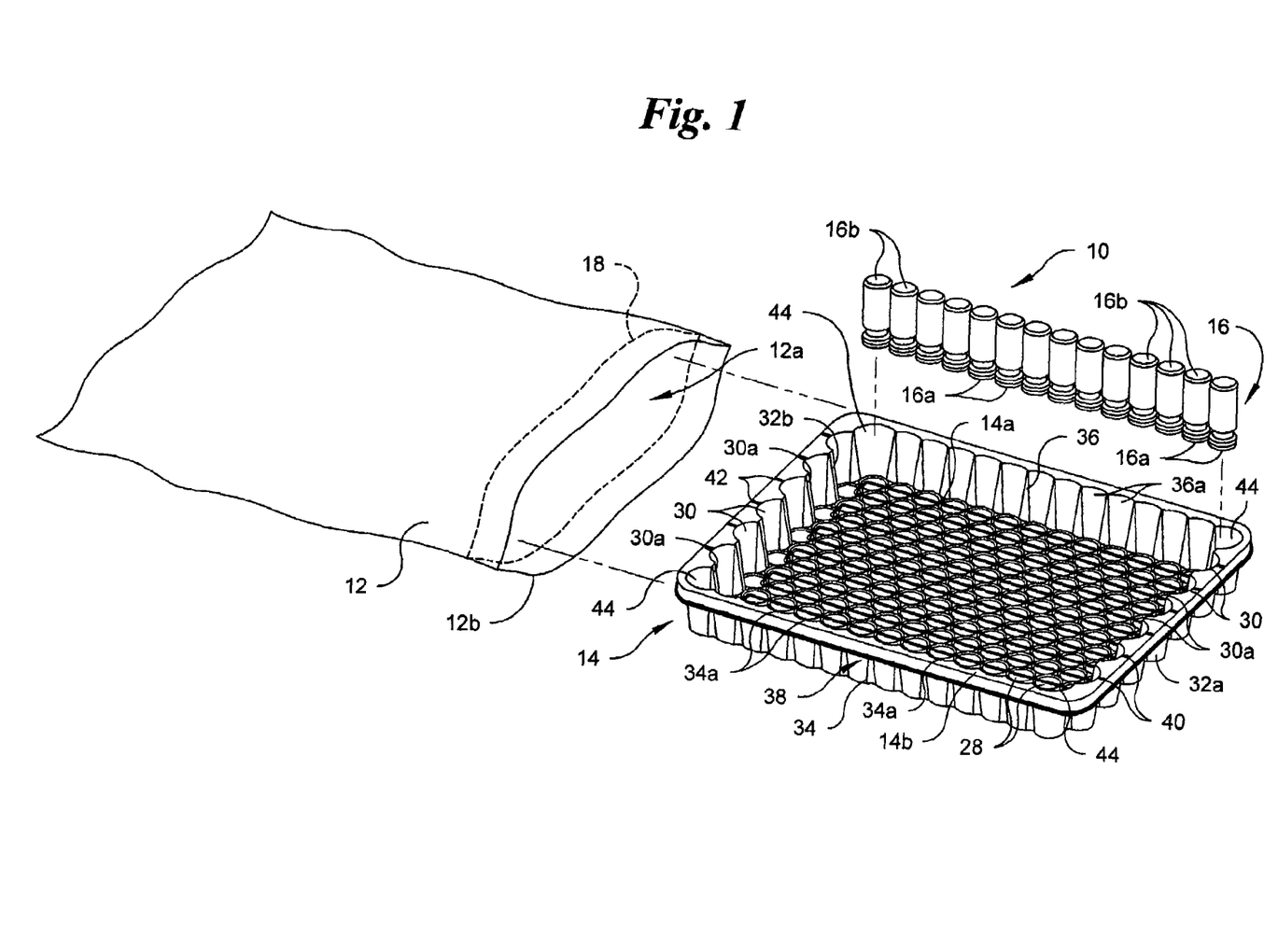
FIG. 1 is an exploded view of a vacuum packaging system including a tray, a row of vials and a vacuum bag in accordance with a first preferred embodiment of the present invention.
Figure 3:
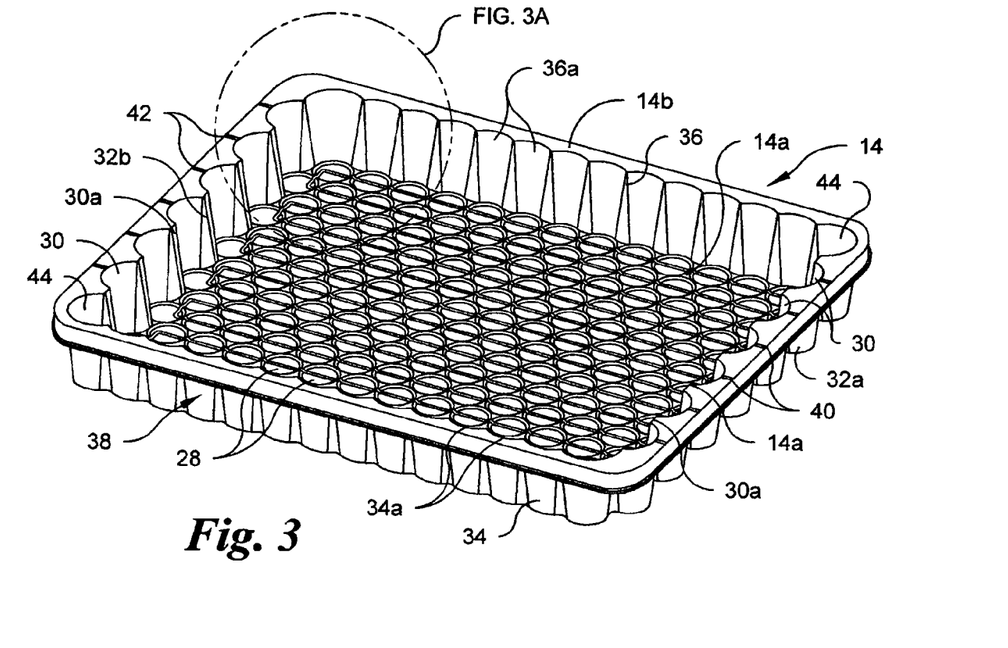
FIG. 3 is a top perspective view of the tray of the vacuum packaging system shown in FIG. 1.
Figure 3A:
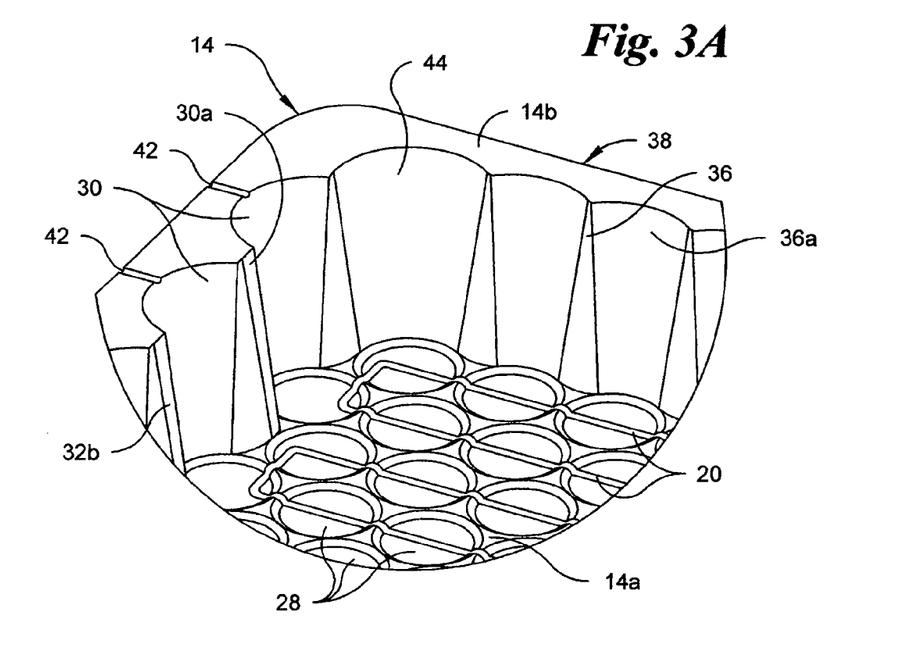
FIG. 3A is magnified, partial top perspective view of the tray of the vacuum packaging system shown in FIG. 1, taken from within the dashed circle of FIG. 3.
Figure 4:
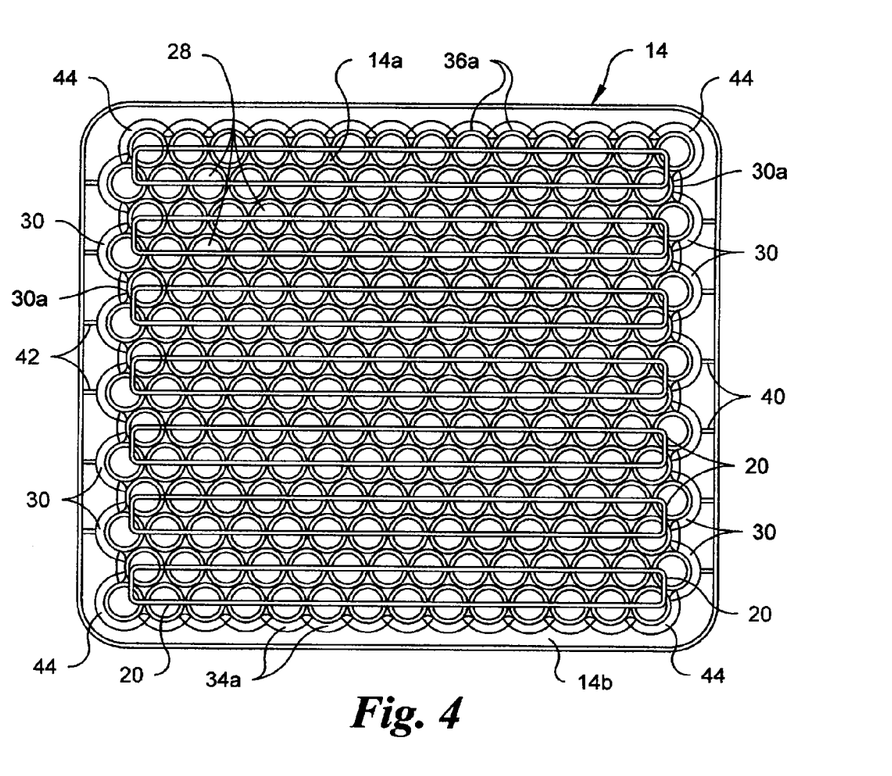
FIG. 4 is a top plan view of the tray of the vacuum packaging system shown in FIG. 1.

Referring to FIGS. 1 and 3-4, in the first preferred embodiment, the tray 14 includes corner pockets 44 at the intersection of the first and second sidewalls 32a, 32b and the front and rear walls 34, 36, respectively. The corner pockets 44 preferably conform to and are in engagement with at least a portion of the external surface of the medical containers 16 that are positioned in corners of the tray 14. Similar to the side pockets 30 and front and rear pockets 34a, 36a, the corner pockets 44 stabilize the rows and columns of medical containers 16 that are positioned in the tray 14. The tray 14 is not limited to the inclusion of the corner pockets 44 and may include corner pockets having nearly any size or shape to accommodate nearly any sized or shaped medical container 16 or may have a generally squared corner. The corner pockets 44 preferably have a generally arcuate shape to accommodate the generally cylindrical vials 16 that are mounted in the tray 14.

Referring to FIGS. 1-4, the tray 14 includes the floor 14a and the top edge 14b opposite the floor 14a with the sidewalls 32a, 32b and front and rear walls 34, 36 therebetween. The plurality of vials 16 is preferably stacked in the tray 14 with a head side 16a in contact with the floor 14a and a base side 16b proximate the top edge 14b. The vials 16 are preferably loaded into the tray 14 in this orientation, typically to accommodate loading of the vials 16 into an assembly line by an operator. Alternatively, the vials 16 may be stacked in the tray 14 with the base side 16b in contact with the floor 14a and the head side 16a adjacent the top edge 14b, typically to accommodate loading of the vials into the assembly line by a robot.

In addition, the vials 16 may be loaded or positioned in the tray 14 such that their sides are in contact with the floor 14a. One having ordinary skill in the art will realize that the vials 16 are not limited to being stacked in the tray 14 in the above-described orientations and may be stacked in nearly any orientation for insertion into the vacuum bag 14. The plurality of vials 16 are preferably stacked relatively tightly in the tray 14 to reduce movement of the vials 16 relative to each other and the tray 14 during movement or shipping of the tray 14.

Referring to FIGS. 1 and 3-4, in the first preferred embodiment, the tray 14 also includes depressions 28 formed in the floor 14a of the tray 14. The depressions 28 preferably conform to the head side 16a and/or base side 16b of the medical container 16 when the containers 16 are positioned in the tray 14 to orient the medical container 16 with respect to the tray 14. The tray 14 preferably includes a plurality of depressions 28, wherein each depression 28 conforms to a single head or base 16a, 16b of a single container or vial 16. In the first preferred embodiment, one hundred ninety-six (196) depressions are formed in the floor 14a to accommodate one hundred ninety-six vials 16 that are positioned within the preferred tray 14. The tray 14 is not limited to inclusion of one hundred ninety-six depressions and may include nearly any number of depressions 28 to accommodate nearly any number of vials or medical containers 16 within the tray 14. In addition, the tray 14 is not limited to the inclusion of depressions 28 and may have a generally planar floor 14 to support the vials 16. The depressions 28 preferably aid in properly orienting the vials 16 within the tray 14.

Figure 8:
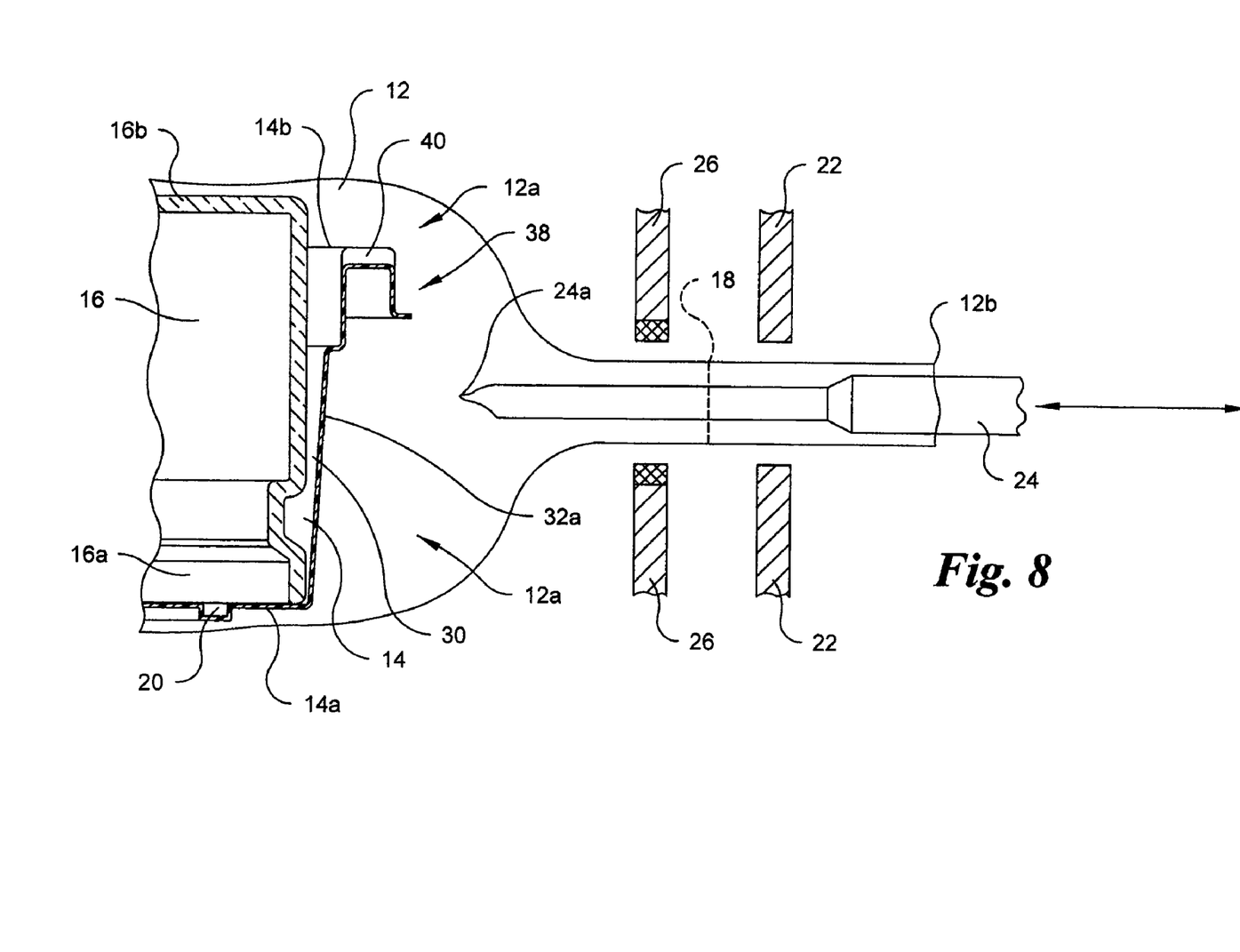
FIG. 8 is a magnified cross-sectional, side elevational view of a vacuum probe partially positioned within the vacuum bag of the vacuum packaging system shown in FIG. 1.

Referring to FIGS. 3, 3A and 8, in the first preferred embodiment, the tray 14 includes a U-shaped peripheral flange 38 formed proximate a mouth of the tray 14. The top edge 14b forms a bottom of the U-shape of the peripheral flange 38 in the first preferred embodiment. The U-shaped peripheral flange 38 provides strength and stiffness to the tray 14 to resist crushing or other failure of the mouth of the tray 14 under loading. For example, the peripheral flange 38 preferably provides strength and stiffness to the tray 14 such that the top edge 14b generally does not deform significantly or buckle when the tray 14 filled with vials 16 is positioned in the internal cavity 12a, a vacuum is drawn from the internal cavity 12a and the bag 12 is sealed. The tray 14 is not limited to the inclusion of the U-shaped peripheral flange 38 and may include nearly any sized and shaped top edge 14b that is able to perform the general functions of the tray 14 and withstand the normal operating conditions of the tray 14. The preferred peripheral flange 38 is integrally molded with the tray 14 but is not so limited and may be comprised of a separate component that is mounted to the tray 14 after construction of the tray 14. Alternatively, the top edge 14b may be rolled or have an increased thickness when compared to the walls 32a, 32b, 34, 36 of the tray 14 to provide stiffness and strength at the top edge 14b. The tray 14 is not limited to the inclusion of the U-shaped peripheral flange 38 and may include a terminal end at the top of the walls 32a, 32b, 34, 36 without stiffening or reinforcement.

Referring to FIGS. 1-4 and 8, in the first preferred embodiment, vents are formed in the peripheral flange 38 and are comprised of a first series of troughs 40 formed in the top edge 14b of the peripheral flange 38 proximate the first sidewall 32a and a second series of troughs 42 formed in the top edge 14b of the peripheral flange 38 proximate the second sidewall 32b. The first and second series of troughs 40, 42 are preferably integrally molded into the peripheral flange 38 at the top edge 14b as arc-shaped cavities. In the first preferred embodiment, each trough 40, 42 is associated with one of the side pockets 30 in the first and second sidewalls 32a, 32b. Accordingly, in the first preferred embodiment, the first sidewall 32a includes six troughs 40 and the second sidewall 32b includes six additional troughs 42. The troughs 40, 42 preferably permit the flow of air or purge gas from or into the tray 14 when a vacuum is drawn or purge gas flows into the internal cavity 12a and the tray 14 is in the internal cavity 12a, as will be described in greater detail below. The tray 14 is not limited to the inclusion of the first and second series of troughs 40, 42 or to the above-described number of troughs 40, 42 in the peripheral flange 38. For example, the vents may be comprised of a plurality of holes in one of the first or second sidewalls 32a, 32b or the front and rear walls 34, 36 or a single or multiple holes formed in the floor 14a of the tray 14. The vents are preferably formed in the tray 14 such that air and/or purge gas may flow out of the tray 14 when a vacuum is drawn from the internal cavity 12a and the tray 14 is in the internal cavity 12a, as will be understood by one having ordinary skill in the art, to permit air and/or purge gas to flow into and out of the tray 14 without being blocked by the flexible film 12.

Referring to FIGS. 3-4 and 8, in the first preferred embodiment, the tray 14 also includes at least one vacuum groove 20 formed in the floor 14a. The vacuum groove 20 is preferably comprised of a channel that traverses the floor 14a and is in contact with each one of the plurality of depressions 28. The vacuum groove 20, similar to the vents, provides a conduit for the release of air and/or purge gas from the medical containers 16 that are positioned in the tray 14 when a vacuum is drawn from the internal cavity 12a. The vacuum groove 20 preferably permits the release of gas or air from the inside of the vials 16 such that air is typically not trapped within the vials 16 when the vacuum is drawn from the internal cavity 12a or purge gas is introduced into the internal cavity 12a. The tray 14 is not limited to the inclusion of the vacuum groove 20 and may not include a vacuum groove 20 or the tray 14 may be include a mound or mounds of material that orient the medical containers 16 such that gas is able to escape from the inside of the containers 16 by providing a gap between at least a portion of the head side 16a relative to the floor 14a when the medical container 16 are positioned in the tray 14. In addition, the vacuum groove 20 may be comprised of individual holes located in the depressions 28 to allow the release of air from inside the containers 16 when a vacuum is drawn from the internal cavity 12a.

Figure 5:
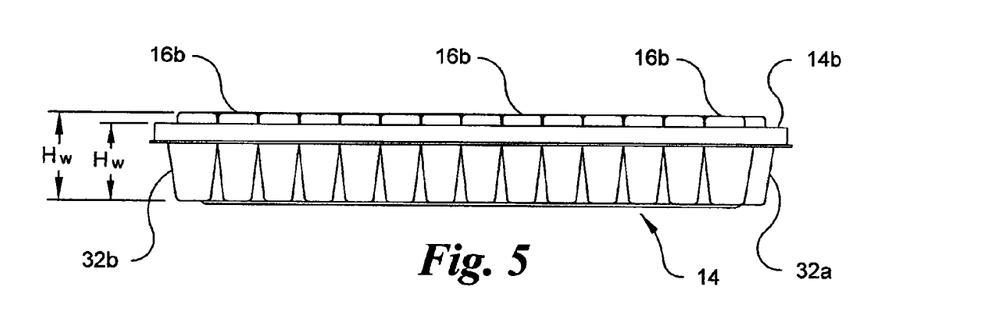
FIG. 5 is a front elevational view of the tray and rows of vials stacked in the tray of the vacuum packaging system shown in FIG. 1.

Referring to FIGS. 5 and 8, in the first preferred embodiment, the base ends 16b of the vials 16 protrude from and above the top edge 14b of the tray 14 when the vials 16 are mounted or stacked in the tray 14. In the first preferred embodiment, the vials 16 have a vial height $H_V$ of approximately two and one-eighth inches (2⅛") resulting in the base ends 16b of the vials 16 protruding from the top edge 14b approximately one-quarter inch (¼"). The vials 16 are not limited to having a vial height $H_V$ of two and one-eighth inches and may have nearly any height that may be accommodated by the tray 14. In addition, the vials 16 are not limited to protruding from the top edge 14b of the tray 14 and may be positioned in the tray 14 such that their base or head ends 16b, 16a are flush with the top edge 14b or are recessed from the top edge 14b. However, it is preferred that the vials 16 protrude from the top edge 14b such that the vacuum bag 12 engages portions of the head end 16a or base end 16b and sides of the vials 16 when the vacuum is drawn from the internal cavity 12a to securely hold the vials 16 in position in the tray 14.

Figure 2:
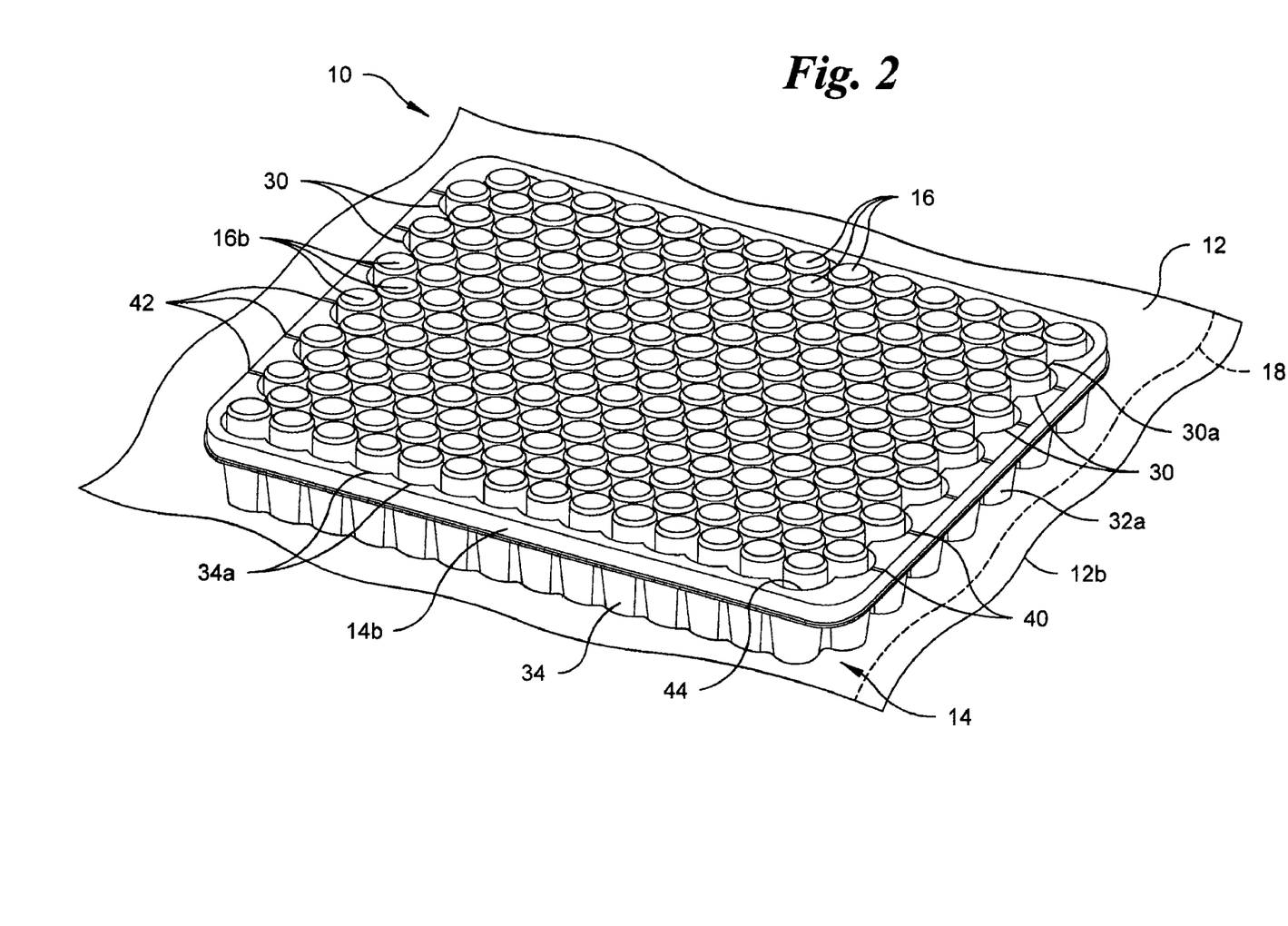
FIG. 2 is a top perspective view of the tray with the vials stacked therein and the tray positioned in the vacuum bag of the vacuum packaging system shown in FIG. 1.

Referring to FIGS. 1, 2 and 8, in the first preferred embodiment, the flexible film 12 is comprised of the vacuum bag 12 having the general shape of a rectangular bag with an open end 12b and the internal cavity 12a. The internal cavity 12a is preferably large enough to encompass the tray 14 when it is filled with the stacked plurality of vials 16. The vacuum bag 12 is preferably constructed of a multi-layer polymer that is resistant to gas permeation, but is not so limited. The vacuum bag 12 is also preferably constructed of a material that is able to be sterilized, depyrogenated, cleaned of non-viable particulate matter and sealed at its open end 12b such that gas does not permeate through the seal. Many types and sizes of vacuum bagging material may be utilized to construct the vacuum bag 12, as will be understood by one having ordinary skill in the art.

The vacuum bag 12 of the preferred embodiments includes a tear notch 18 (FIG. 2) that accommodates opening of the vacuum bag 12 after it has been positioned around the tray 14 and vials 16, evacuated and sealed. The tear notch 18 simplifies opening of the vacuum packaging system 10 to permit an end user to access the tray 14 and vials 16. One having ordinary skill in the art will realize that the notch 18 is provided for opening convenience and is not required for the operation of the vacuum packaging system 10. The tear notch 18 is preferably an initiation notch that provides a sharp notch to begin a tear to open the vacuum bag 12, but may be constructed of a low strength line or partially perforated line in the vacuum bag 12 that provides an area to tear open the sealed vacuum bag 12. The preferred vacuum bag material is oriented such that the tear will proceed from the tear notch 18 along a line generally perpendicular to a side edge of the vacuum bag 12. Vacuum bag materials having this characteristic are known to those having skill in the vacuum bag art. The vacuum bag 12 may not include the tear notch 18 and would continue to function, as would be understood by one having ordinary skill in the art.

In operation, in the first preferred embodiment, the medical containers or vials 16 are molded and at the conclusion of the molding operation, the vials 16 are relatively pyrogen free and non-viable particulate matter free. The vials 16 are inserted into the tray 14 in this condition, preferably such that at least a portion of the vials 16 and most preferably such that the base end 16b extends above the top edge 14b. The tray 14 is also preferably sterile, pyrogen free and non-viable particulate matter free when the vials 16 are inserted therein. The tray 14 is inserted into the internal cavity 12a and the internal cavity 12a is evacuated to a predetermined vacuum pressure such that the flexible film 12 surrounds and engages the tray 14 and at least portions of the medical containers 16. Specifically, the flexible film 12 preferably engages the base ends 16b of the vials 16 and portions of the side surfaces, which extend out of the mouth of the tray 14 and exposed surfaces of the tray 14 under the force of external air pressure. The flexible film 12 is then sealed such that the predetermined vacuum pressure is generally maintained in the internal cavity 12a. The sealed flexible film 12 with the tray 14 and plurality of vials 16 therein may be transported without significant movement of the vials 16 because the atmospheric pressure on the flexible film 12 consolidates and holds the vials 16 in position in the tray 14. Accordingly, the vials 16 generally do not move during shipment, reducing the likelihood that the vials 16 rub up against each other and potentially damage each other. In addition, if the vials 16 and tray 14 are sterilized, non-viable particulate matter free and pyrogen free when they are inserted into the internal cavity 12a, the vials 16 and tray 14 are also generally in the same condition when the vacuum bag 12 is opened, assuming the predetermined vacuum pressure is retained in the internal cavity 12a.

In the first preferred embodiment, the vials 16 are inserted into the tray 14 by grasping one or more of the vials 16 with a mechanical or robotic arm (not shown) as the vials 16 flow off of a medical container molding assembly line. The mechanical arm is preferably associated with a robot that is able to place the vial 16 or a plurality of vials 16 into the tray 14 such that the vials 16 are positioned in rows within the tray 14 and each vial 16 is associated with a specific depression 28. Specifically, once the medical containers or vials 16 are molded by the medical container molder, the containers 16 are preferably handled exclusively by robots to limit exposure of the containers 16 to contaminants or pyrogens before they are filled with a medical product. Prior to inserting the container 16 into the tray 14, the container 16 is preferably robotically transported to an inspection station for dimensional and quality inspection. Inspection preferably determines whether the container 16 has an acceptable dimensional shape because improperly sized and/or shaped containers 16 may not properly stack within the tray 14 and may be unusable by a customer. The containers 16 are preferably positioned in the tray 14 such that their head sides 16a are in facing engagement with the depressions 28 and their base sides 16b protrude above the top edge 14b of the tray 14.

In the first preferred embodiment, the vials 16 are robotically inserted into the tray 14 in a series of fourteen (14) rows between the first and second sidewalls 32a, 32b. The first row of vials 16 preferably includes fourteen vials 16 that are associated with individual depressions 28 proximate the front or rear walls 34, 36. The end vials 16 in the rows are mounted such that they are within or conform to the shape of the corner pockets 44 and the twelve vials 16 in the middle of the row are associated with the front or rear pockets 34a, 36a on the front or rear walls 34, 36. A second row of vials 16 is then inserted into the tray 14 immediately adjacent the first row with one of the end vials 16 associated with one of the side pockets 30 and an opposing vial 16 on an opposite end of the row associated with one of the peaks 30a. Each of the vials 16 in the second row is also associated with a depression 28. The additional rows of vials 16 are similarly inserted into the tray 14 until the tray 16 is completely filled with vials or other medical containers 16. The vials 16 are not limited to being inserted into the tray 14 in rows and may be individually inserted into the tray 14 in a random pattern or may all be inserted into the tray 14 at one time. However, it is preferred that the vials 16 are positioned or stacked in the tray 14 in the manner shown in FIG. 2 such that the vials 16 are closely stacked in the tray 14 to generally prevent significant movement of the vials 16 during movement or shipping.

Referring to FIGS. 1, 2 and 8, as was described above, after the vials 16 are positioned in the tray 14, the tray 14 is inserted into the internal cavity 12a of the flexible film or vacuum bag 12. As was also described above, the vials 16 are preferably relatively pyrogen free and non-viable particulate matter free when they are positioned in the tray 14 and inserted in the internal cavity 12a. A vacuum probe 24 is inserted into the open end 12b such that a tip 24a of the probe 24 is in communication with the internal cavity 12a. A purge gas is introduced into the internal cavity 12a by the vacuum probe 24 and air is forced out of the internal cavity 12a. Sealing jaws 26 engage the open end 12b of the vacuum bag 12 such that additional air or purge gas generally does not escape or enter the internal cavity 12a through the open end 12b. The vacuum probe 24 is then actuated to draw a vacuum in the internal cavity 12a, thereby drawing the purge gas and air out of the internal cavity 12a such that the pressure within the internal cavity 12a is reduced to a predetermined vacuum pressure. As the vacuum is drawn from the internal cavity 12a, external air pressure urges the flexible film or vacuum bag 12 against the tray 14 and the vials 16. As the external pressure becomes higher, the vacuum bag 12 adheres relatively tightly to surfaces of the tray 14, preferably preventing movement of the vials 16 relative to the tray 14 or each other. The first and second series of troughs 40, 42 provide a conduit for air to escape the inside of the tray 14 as the film or bag 12 tightly adheres to the surfaces of the tray 14 such that additional vacuum can be drawn because the flexible film or bag 12 generally bridges over the troughs 32a, 32b providing a flow channel for the purge gas and air to escape from the internal cavity 12a. In addition, the vacuum groove 20 permits purge gas and/or remaining air to escape from inside the individual vials 16 because the head side 16a of the vial 16 is not in complete facing engagement with or sealed to the floor 14a of the tray 14. For example, if the floor 14 were flush, the head side 16a of the vial 16 may completely engage and create a seal with the planar floor 14a. If the head side 16a of the vial 16 is sealed, purge gas and air may be sealed within the vial 16 because no gap or conduit is provided for the escape of gas from the vial 16 and this gas may subsequently escape from the vial 16, potentially compromising the vacuum in the bag 12.

After the vacuum has been drawn in the internal cavity 12a to a predetermined level, sealing jaws 26 engage the flexible film or vacuum bag 12 proximate the open end 12b and preferably heat seal the vacuum bag 12 to maintain the vacuum within the internal cavity 12a. Because the predetermined vacuum is maintained in the internal cavity 12a, the vacuum bag 12 continues to adhere to the tray 14 and portions of the vials 16 to consolidate and hold the vials 16 in the tray 14, generally to prevent significant movement of the vials 16 relative to the tray 14 and rubbing of the vials 16 against each other. The vacuum probe 24 is removed from the internal cavity 12a and the vacuum bag 12 is also sealed at the entrance for the vacuum probe 24. The clamp jaws 22 and sealing jaws 26 release the vacuum bag 12 and the vacuum bag 12 is inspected to check for any leaks in the bag 12. If leaks are detected, the vacuum bag 12 may be repaired or discarded and the tray 14 may be inserted into another vacuum bag 12. If the predetermined vacuum pressure is maintained in the internal cavity 12a, the vials 16 generally maintain their sterile, pyrogen free and non-viable particulate matter free condition and do not significantly move or rub against each other during shipping or other movement because of the tight adherence of the vacuum bag 12 to the external surfaces of the vials 16 and tray 14.

Referring to FIG. 2, in the first preferred embodiment, the sealed vacuum bag 12 with the tray 14 and plurality of vials 16 are preferably irradiated to sterilize the bag 12, tray 14 and vials 16. The bag 12, tray 14 and vials 16 are preferably irradiated for sterilization because the material of the polymeric materials of the bag 12, tray 14 and vials 16 is typically unable to withstand high temperatures that would be required to bake or otherwise heat the bag 12, vials 16 and tray 14 to remove pyrogens and sterilize. Irradiation of the sealed bag 12, tray 14 and vials 16 is not limited and this step may be completely eliminated from the process if the vials 16, tray 14 and bag 12 are otherwise conditioned for sterilization prior to being inserted into the bag 12.

Referring to FIGS. 1 and 2, in the first preferred embodiment, the sealed and evacuated vacuum bag 12 with the sterile, pyrogen free and non-viable particulate matter free tray 14 and plurality of vials 16 mounted therein is preferably transported to a medical container filler such that the vials 16 can be filled with some type of fluid, preferably medication, saline or another medical product. Often, the assembly is transported as air cargo and is subjected to the reduced air pressure that is common during air travel. Accordingly, the predetermined vacuum within the vacuum bag 12 is preferably near or below the reduced pressure that is typically encountered during air travel. If the vacuum pressure in the bag 12 is not below this pressure, the consolidation of the vials 16 may be at least partially compromised by the bag 12 releasing from some surfaces of the tray 14 and vials 16, permitting the vials 16 and/or tray 14 to move within the bag 12. If the vacuum bag 12 releases from the tray 14 and vials 16, the vials 16 may move within the tray 14 and rub against each other, potentially damaging the vials 16. When the vacuum packaging assembly arrives at its destination, the vacuum bag 12 is preferably inspected to ensure that the bag 12 is engaged with the tray 14 and at least portions of the vial 16 indicating that the predetermined vacuum pressure within the internal cavity 12a has been maintained during shipping. Assuming the inspection reveals that the predetermined vacuum pressure has been maintained within the vacuum bag 12, the vacuum bag 12 is opened to gain access to the tray 14 and medical containers 16. The tray 14 is removed from the internal cavity 12a and the medical containers or vials 16 are removed from the tray 14, preferably robotically, for introduction onto an assembly line for filling the vials 16. If the predetermined pressure is maintained within the internal cavity 12a, medical products may be inserted into the vials 16 under the general assurance that the vials 16 and tray 14 are sterile, non-viable particulate matter free and pyrogen free. However, if the predetermined pressure is not maintained in the internal cavity 12a, the inspection typically reveals a breach in the bag 12, which may result in a necessity to sterilize, remove non-viable particulate matter and/or remove pyrogens from the vials 16 and tray 14 before introducing the tray 14 and/or vials 16 to a clean room environment or otherwise filling the vials 16 with medical products.

In the first preferred embodiment, the vacuum bag 12 preferably includes the tear notch or tear perforation 18 proximate the open end 12b. The tear notch or perforation 18 may be utilized to tear open the vacuum bag 12 to gain access to the tray 14 and vials 16. The vacuum bag 12 is not limited to the inclusion of the tear notch and/or tear perforation 18 and may include nearly any line of weakness or stress riser to provide an advantage for the filler to open the vacuum bag 12 or may include none of the these features. Specifically the vacuum bag 12 may be opened by cutting the vacuum bag 12 without use of a tear perforation 18.

In an alternative method, after the tray 14 and vials 16 are removed from the vacuum bag 12 by an operator, a rigid sheet (not shown) may be positioned onto the base side 16b of the vials 16. The operator or a robot may then invert the tray 14, vials 16 and rigid sheet and place the rigid sheet on a support surface (not shown) such that the base side 16b is resting on the rigid sheet. The rigid sheet is then moved out from under the vials 16 such that the base side 16b is resting on the support surface and the tray 14 maintains the vials 16 in their consolidated configuration. The tray 14 may then be vertically removed from the vials 16 such that the head side 16a is exposed and the vials 16 may be grasped for introduction onto an assembly line. Another alternative would be to insert the vials 16 into the tray 14 with their head side 16a proximate a floor 14a of the tray 14. When the vials 16 and tray 14 are ready to be removed from the vacuum bag 16, the vacuum bag 16 would be inverted with the base side 16b of the vials facing the support surface (not shown). The tray and vials would then be moved out of a tear in the bag 16 such that the base side 16b of the vials 16 are in facing engagement with the support surface. The tray 14 would then be vertically moved away from the vials 16 such that the head side 16a is exposed and the vials 16 may be grasped for introduction onto an assembly line.

Alternatively, referring to FIGS. 2-4, in operation, the plurality of vials 16 may be sterilized and positioned in the sterilized tray 14 with the head side 16a or base side 16b adjacent the floor 14a, potentially depending upon whether the vials 16 will be inserted into the assembly line manually or by a robot. The tray 14 with the stacked vials 16 positioned therein is inserted into the internal cavity 12a of the vacuum bag 12. The vacuum bag 12 is then transported to a sealing mechanism, which includes the clamp jaws 22, the vacuum probe 24 and the sealing jaws 26. The clamp jaws 22 close over the open end 12b and the vacuum probe 24, creating an air tight seal at the open end 12b. The vacuum probe 24 is connected to a vacuum source (not shown) and is actuated to evacuate air from the internal cavity 12a until a predetermined vacuum is reached. The vacuum bag 12 conforms to the exposed shape of the tray 14 and stacked vials 16 indicating a vacuum is being created within the vacuum bag 12. The pressure of the vacuum bag 12 on the external surfaces of the vials 16 and tray 14 preferably hold the vials 16 in the tray 14 such that the vials 16 do not rub against each other during movement or shipping. The peripheral flange 38 provides stiffness to the tray 14 so that the tray 14 is not crushed when the vacuum bag 12 is evacuated. When the predetermined vacuum is reached, the vacuum probe 24 is withdrawn from the open end 12b and the sealing jaws 26 are simultaneously closed over the open end 12b. The sealing jaws 26 create an air-tight seal across the open end 12b, preferably through a heat seal. The vacuum package system 10 is then irradiated and prepared for transport to an end user, typically a manufacturer who will fill the medical containers 16 with a medical product. Assuming the vacuum bag 12 is not breached during shipment, the vials 16 and tray 14 are sterile, pyrogen free and non-viable particulate matter free when they reach the manufacturer and may be introduced directly onto an assembly line in a clean environment.

The vacuum package system 10 generally prevents chafing and scratching of the plurality of vials 16 against one another during transport by consolidating the vials 16 due to the pressure applied to the tray 14 and vials 16 by atmospheric pressure outside the vacuum bag 12. Chafing or scratching of the vials 16 may produce unacceptable particles and damage surface finish making the vials 16 unsafe and useless for receipt of medical products. The vacuum package system 10 also preferably counteracts the impact of reduced atmospheric pressure, which the vacuum package system 10 may encounter during transportation by aircraft, during land transport at high elevations or in nearly any conditions where the vacuum package system 10 is exposed to reduced atmospheric pressure, as was described above. A typical sealed container that is filled with vials 16 may be subjected to reduced atmospheric pressure during aircraft or high elevation transportation that may be significant enough to cause an unvented package with approximately sea level pressure inside to expand to the point that seams are stressed and burst. Because the vials 16 of the vacuum package system 10 are stored under vacuum, the reduced atmospheric pressure has little or no effect upon the vacuum bag 12 and vials 16 of the preferred embodiments. Further, the use of the vacuum package system 10 provides a ready indicator of a breach in the vacuum bag 10 to the end user. If the vacuum bag 12 is breached during transport or prior to reaching the end user, the vacuum bag 12 will not thereafter cling or conform to the shape of the tray 14 and/or vials 16. Accordingly, an end user is aware that there has been a breach of the vacuum package system 10 and the sterile, pyrogen free and particulate matter free condition of the vials 16 may have been compromised. However, if the vacuum bag 12 is not breached, the end user is aware that the vials 16 are generally sterile, pyrogen free and non-viable particulate matter free and may be introduced directly into an assembly operation for filling the vials 16 with medical products.

When the unbreached vacuum package system 10 reaches a user, the user grasps the vacuum bag 12 on either side of the tear notch 18 and rips the vacuum bag 12 open. Inclusion of the tear notch 18 allows the vacuum bag 12 to be opened without the use of tools or the generation of particles that may contaminate the vials 16 during a cutting operation. The vacuum package system 10 is typically opened in a clean room to maintain sterility of the vials 16. The tray 14 and vials 16 are removed from the open end 12b and a sterile, pyrogen free and non-viable particulate matter free rigid sheet (not shown) that covers the open end of the tray 14 is placed on the assembly such that the base sides 16b of the vials 16 are in contact with the sheet. The entire assembly is inverted such that the vials 16 are resting on the sheet. The assembly is placed onto the support surface and the sheet is removed laterally from beneath the stacked vials 16, leaving the vials 16 resting on the surface on their base side 16b. The tray 14 is then removed vertically leaving the plurality of stacked vials 16 standing on the surface for manual insertion into the filling machine. Alternatively, the tray 14 is stacked with vials 16 having their base sides 16b adjacent the floor 14a. The tray 14 and stacked vials 16 are removed from the vacuum bag 12 and are positioned on the support surface with the floor 14a adjacent the surface. The vials 16 may then be removed directly from the tray 14 and placed onto an assembly line for filling the vials 16 with medical products, preferably by a robot. One having ordinary skill in the art will realize that the above-described methods of stacking and processing the vials 16 are not limiting and the vials 16 may be stacked in the tray 14 in nearly any configuration and processed in nearly any manner once the tray 14 and vials 16 are removed from vacuum bag 12 in preparation for the introduction of medical products therein. The above-described stacking and processing methods are merely provided as examples of typical stacking and processing techniques.

Figure 6:
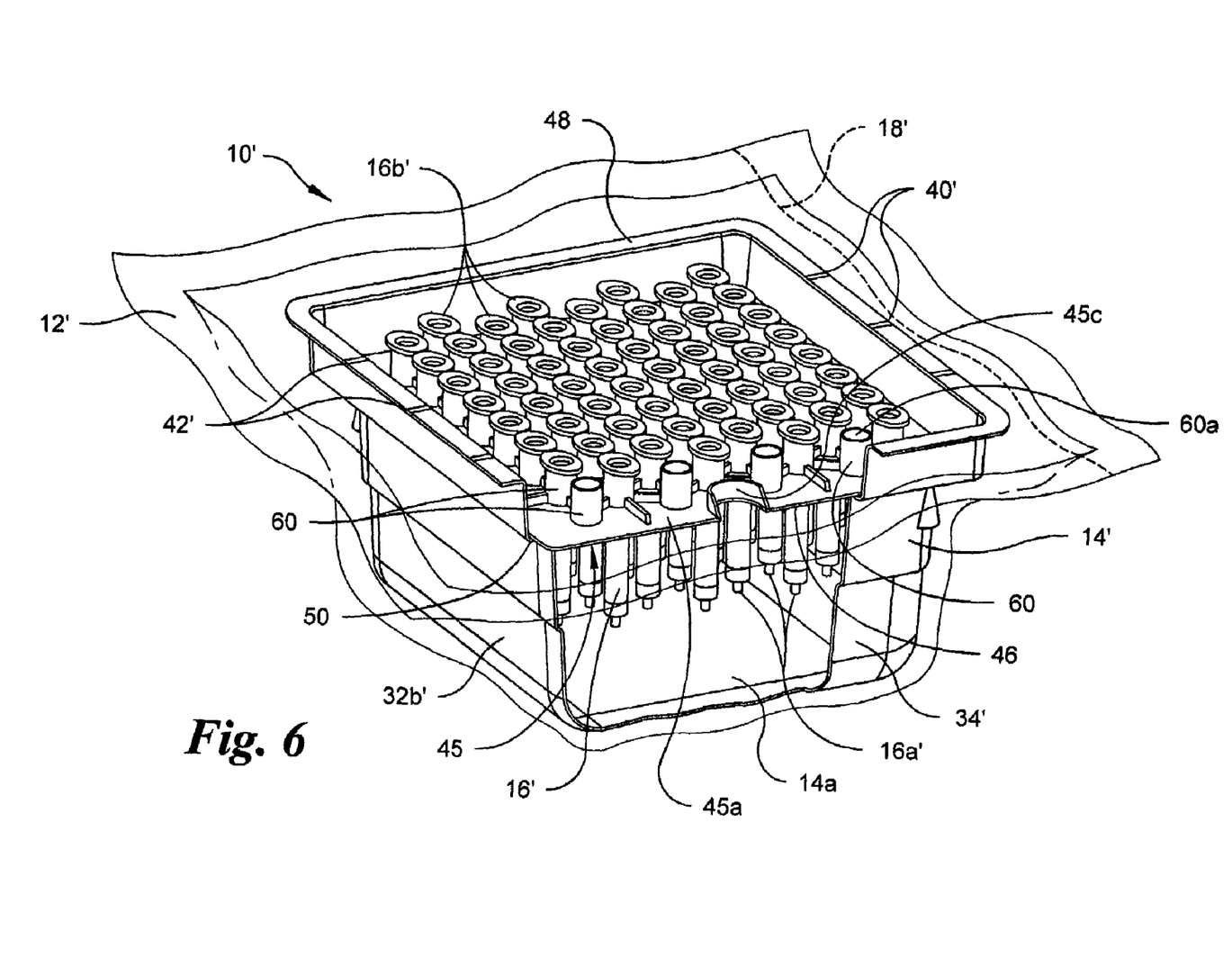
FIG. 6 is a top perspective, partial fragmentary view of a vacuum packaging system including a plurality of syringes mounted on a nesting plate in a tray that is positioned within a vacuum bag in accordance with a second preferred embodiment of the present invention.
Figure 7:
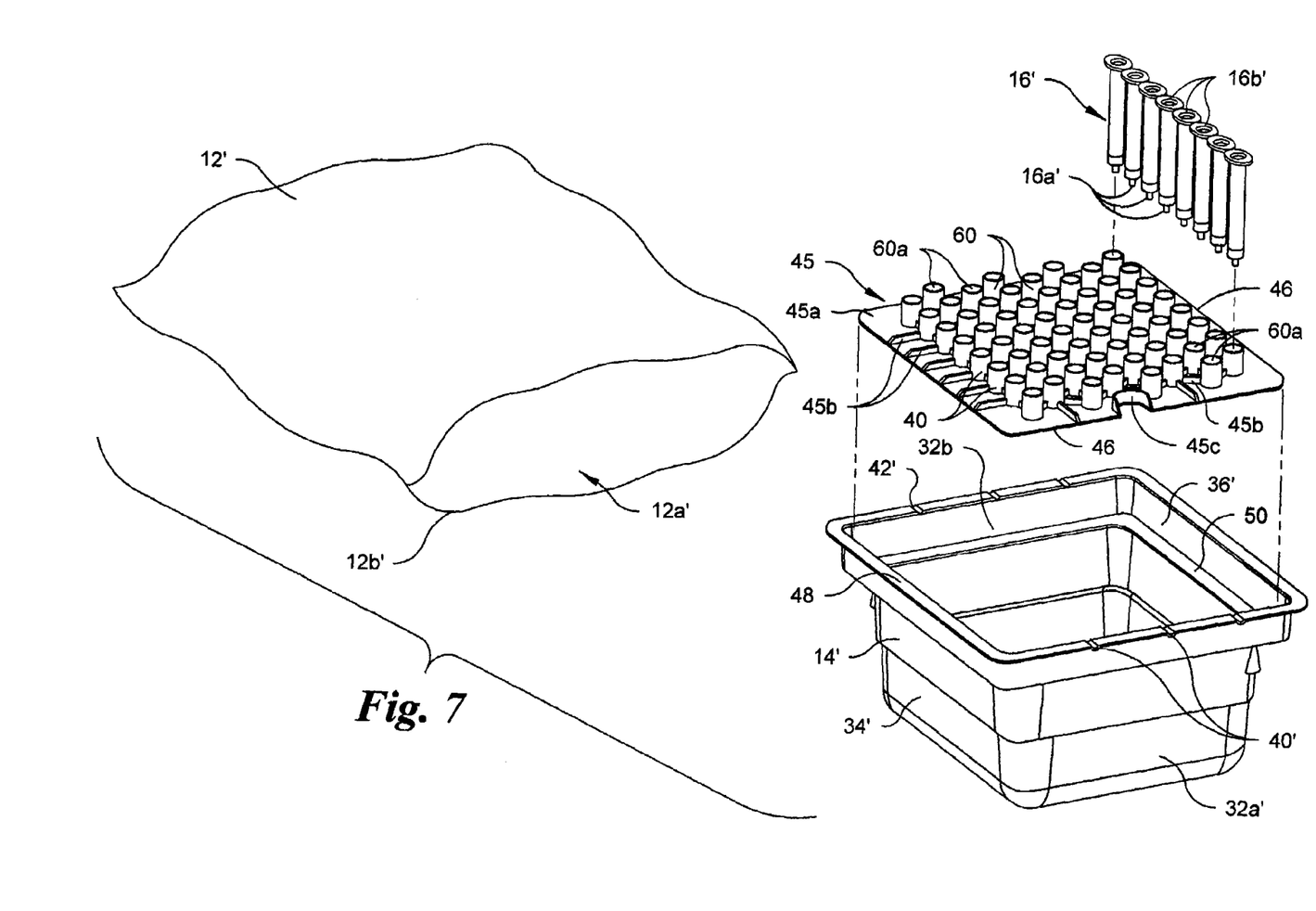
FIG. 7 is an exploded view of the vacuum packaging system shown in FIG. 6.
Figure 7A:
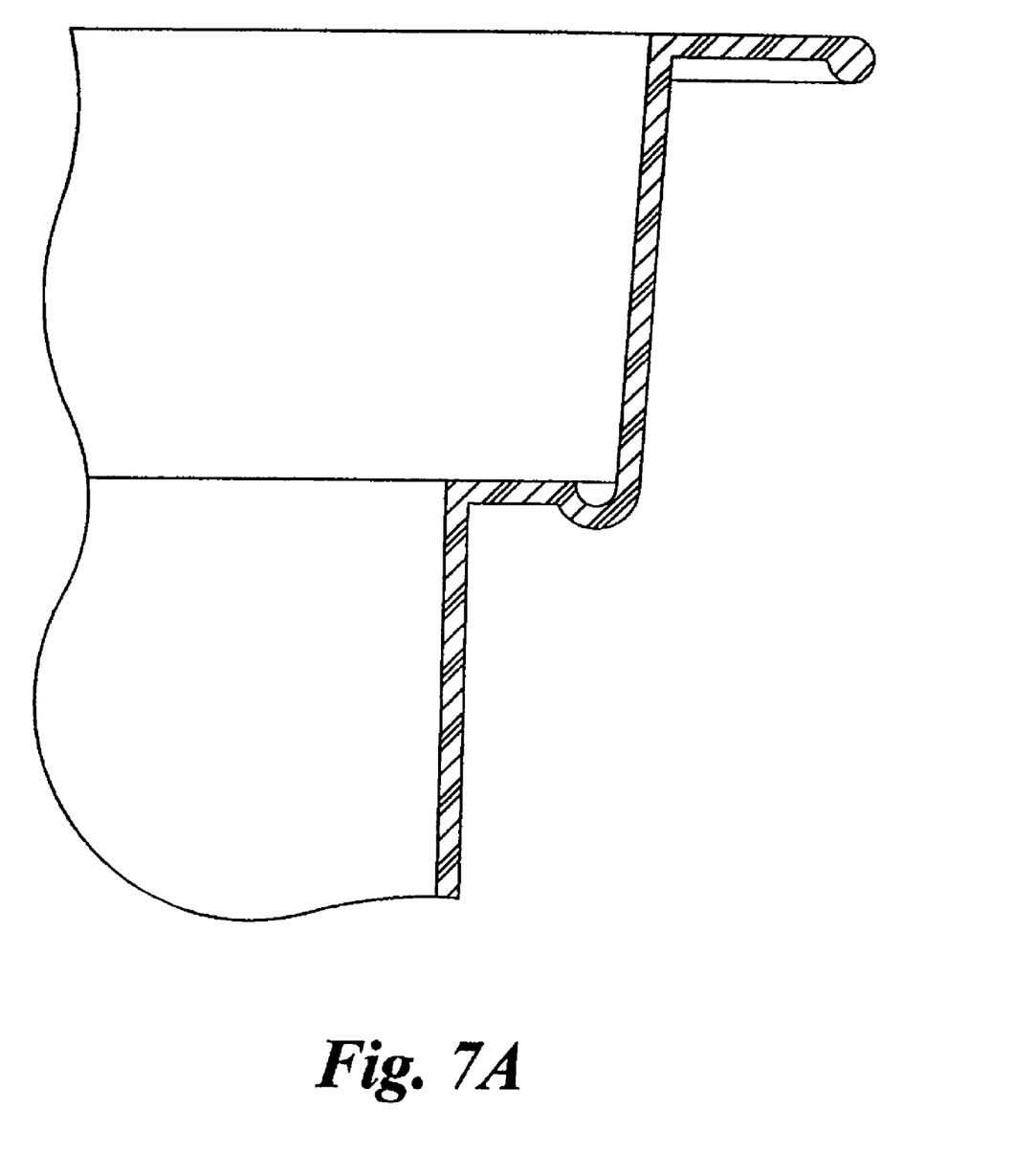
FIG. 7A is a partial cross-sectional view of the tray of the vacuum packaging system shown in FIG. 6, taken along line 7A-7A of FIG. 7.

Referring to FIGS. 6-7A, in a second preferred embodiment, like numerals are utilized to identify like elements and a prime symbol (') is utilized to distinguish like components of the vacuum package system 10' of the second preferred embodiment from the vacuum package system 10 of the first preferred embodiment. In the second preferred embodiment, the medical containers 16' are comprised of syringes 16' that are positioned within the tray 14' for shipping or other transport. The vacuum packaging system 10' preferably permits shipping of the syringes 16' in a ready-to-use condition that is sterile, pyrogen free and non-viable particulate matter free, similar to the above-described vacuum package system 10 of the first preferred embodiment. The syringes 16' have the head side 16a' and the base side 16b', with the base side 16b' including a flange.

In the second preferred embodiment, the tray 14' is constructed of an injection molded polymeric material to form the general size and shape of the tray 14'. The tray 14' is not limited to being injection molded using a polymeric material and may be constructed of a thermoformed plastic material or a machined material, as long as the tray 14' is able to take on its general size and shape and withstand the normal operating conditions of the tray 14'.

The syringes 16' are generally constructed of a high grade polymeric or plastic material that is desirable in the marketplace because of a high resistance to breakage, low chemical extractables and a reduced weight when compared to similar glass syringes. The syringes 16' are typically designed to be used in pre-filled applications and are packaged in generally rigid polymeric trays 14'. In the trays 14', the syringes 16' are preferably mounted in an upright orientation by a nesting plate 45, which is typically constructed of a generally rigid, polymeric material. The nesting plate 45 has a plurality of holes 60a defined by cylindrical sleeves 60. The cylindrical sleeves 60 preferably releasably receive one of the plurality of syringes 16' and hold an empty syringe 16' in a vertical orientation in the tray 14'. The syringes 16' are positioned in the cylindrical sleeves 60 such that the flange at the base end 16b' rests on a top end of the sleeves 60. The syringes 16' are preferably oriented, generally perpendicularly to a plane of a generally planar base 45a of the nesting plate 45. This arrangement of the syringes 16' in the tray 14' is generally known to one having ordinary skill in the art. The array of syringes 16' generally have common center to center distances such that robotic handling equipment is able to remove and insert the syringes 16' from and into the nesting plate 45.

Glass syringes 16' packed in the nesting plate 45 and tray 14', in the manner shown in FIG. 6, are typically sealed in the tray 14' with a permeable lid (not shown) that allows the penetration of a sterilant vapor and can be peeled back to gain access to the glass syringes 16'. This same packaging and sterilization method is not practical for polymeric syringes 16' because the polymeric material has a tendency to absorb the sterilant and release it very slowly. In addition, utilizing the permeable lid does not prevent the external surfaces of the tray 14' from being exposed to the external environment during shipping. Exposure of the external surfaces of the tray 14' to the external environment generally prevents an operator from introducing the tray 14' into a clean environment because of the potential for contamination. High quality polymeric or plastic syringes 16' can be effectively sterilized by irradiation, penetrating gamma or e-beam radiation and, therefore, do not need the permeable packaging. A non-permeable package, however, is subject to the effects of changing atmospheric pressure, much as was described above for the vacuum package system 10 of the first preferred embodiment. Part of the package function is to contain the syringes 16' in the nesting plate 45 within the tray 14' to reduce movement of the syringes 16' and maintain the syringes 16' in a sterile, pyrogen free and non-viable particulate matter free condition until they are ready to be filled with medical products. If a non-permeable package expands due to reduced atmospheric pressure encountered primarily during air shipment or alternate high elevation shipment, the package will no longer hold the syringes 16' in position in the nesting plate 45, potentially resulting in rubbing of the syringes 16' against the nesting plate 45 or bumping in to each other. A secondary effect is that the package may be stressed at weld points or other stress risers and may rupture during shipping. A rupture of the package would cause a leak and the sterility of the contents would likely be compromised.

A solution for this application is to apply a vacuum package using the flexible film or vacuum bag 12', as was described for the first preferred embodiment. A multi-layer film comprised of at least one layer with very low gas permeability is fashioned into the vacuum bag 12'. The tray 14' containing the syringes 16' mounted in the nesting plate 45 is placed into the vacuum bag 12' and the bag 12' is evacuated and sealed, as was described above. With the air removed, the bag 12' clings tightly to the tray 14' and the upper end or flanges of the syringes 16' holding them firmly in the nesting plate 45. The negative effects of reduced atmospheric pressure are counteracted because the bag 12' generally will not loosen its grip on the syringes 16' until the pressure on the inside of the bag 12' equals the pressure on the outside of the bag 12'. For this reason it is desirable to reach a level of vacuum inside the bag 12' at least equal or nearly equal to the pressure encountered in aircraft shipment which is typically eight inches of mercury (8 in. Hg) below standard atmospheric or equivalent to eight thousand feet (8,000 ft.) above sea level. Held tightly in the nesting plates 45, the syringes 16' are less likely to be scratched by contact with the nesting plate 45 and other packaging materials. The vacuum in the bag 12' also serves as a ready indicator of package integrity since even the slightest leak or breach will cause the bag 12' to relax, which will be visually apparent to an operator inspecting the bag 12'. A bag 12' with a leak would thus be readily identified visually as having been breached. Further, maintenance of the vacuum pressure in the bag 12' indicates that the tray 14' and its external surfaces have maintained their sterile, pyrogen free and non-viable particulate matter free condition.

In the second preferred embodiment, the nesting plate 45 includes a generally planar base 45a and reinforcing ribs 45b extending generally perpendicularly from the base 45a. The reinforcing ribs 45b preferably extend from peripheral edges 46 of the nesting plate 45 toward the cylindrical sleeves 60 to provide stiffness and strength to the planar base 45a. An arcuate shaped edge rib 45c also extends generally perpendicularly from the planar base 45a and defines an edge hole. The edge hole is preferably included in the nesting plate 45 such that a user is able to insert a finger or tool through the edge hole to remove the nesting plate 45 from the tray 14'. The edge rib 45c provides stiffness and strength for the base 45a proximate the edge hole. The edge hole and edge rib 45c are not limited to inclusion in the edge of the base 45a and may be positioned at nearly any location on the nesting plate 45 and are not limited for inclusion on the nesting plate 45. The cylindrical sleeves 60 preferably define holes 60a through the nesting plate 45 that are sized and shaped to accept the syringes 16'. The nesting plate 45 is not limited to the inclusion of the reinforcing ribs 45b or the cylindrical sleeves 60. For example, the nesting plate 45 may be constructed of a generally planar plate with holes formed therein for receipt of the syringes 16'. However, the cylindrical sleeves 60 and ribs 45b are preferred for inclusion in the nesting plate 45 to properly orient and space the syringes 16' relative to the nesting plate 45 and to provide strength and stiffness for the nesting plate 45 when the assembly is inserted into the internal cavity 12a' and the vacuum is drawn from the internal cavity 12a'.

In the second preferred embodiment, the tray 14' includes a mouth 48 and a lip 50 proximate the mouth 48. The mouth 48 preferably includes a rounded peripheral bulb 48a at its peripheral edge that provides stiffness to the mouth 48 and provides an arcuate surface for the vacuum bag 12' to engage when a vacuum is drawn on the internal cavity 12a'. A sharp edge at the rounded peripheral bulb 48 could potentially breach the bag 12' when a vacuum is drawn from the internal cavity 12a' exposing the tray 14' and syringes 16' to external air. The peripheral edge 46 of the nesting plate 45 is positioned on the lip 50 to support the nesting plate 45 within the tray 14' in an assembled configuration. The lip 50 is provided to vertically support the nesting plate 45 above the floor 14a' and to generally space the head side 16a' of the syringe 16' from the floor 14a'. The lip 50 is preferably integrally formed in the walls 32a', 32b', 34', 36' of the tray 14'. The lip 50 preferably includes a stiffening groove 50a that provides stiffness to the lip 50 and tray 14' such that the force of the bag 12' against the lip 50 does not significantly deform or crush the lip 50 or tray 14'. The tray 14' is not limited to inclusion of the lip 50 to support the tray 14' or the specific shape and configuration of the lip 50 including the stiffening groove 50a shown in the drawings. For example, the nesting plate 45 may be mechanically fastened, clipped, bonded or otherwise mounted to the tray 14'. In addition, the nesting plate 45 may include legs (not shown) that support the plate 45 above the floor 14a'.

In operation, the vacuum packaging system 10' of the second preferred embodiment is utilized in a similar manner to the vacuum packaging system 10 of the first preferred embodiment. A difference between the two systems is that, during operation, the nesting plate 45 is inserted into the tray 14' such that the peripheral edge 46 of the nesting plate 45 is positioned on the lip 50. The syringes 16' are then inserted into the holes 60a such that the flange on the base end 16b' is in facing engagement with the top of the cylindrical sleeve 60 and the head end 16a' is positioned proximate the floor 14a'. A lid (not shown) may be engaged with the mouth 48 of the tray 14' to close the mouth 48, however, the lid is not necessary for the operation of the vacuum packaging system 10', as will be understood by one having ordinary skill in the art. The tray 14' is positioned into the internal cavity 12a' of the vacuum bag 12' and the internal cavity 12a' is purged and evacuated to the predetermined vacuum pressure using the vacuum probe 24. The troughs 40', 42' provide a conduit for the purge gas and/or air to exit the tray 14' as the vacuum bag 12' collapses onto the mouth 48. However, the tray 14' is not limited to the inclusion of the troughs 40', 42' and may have a generally planar mouth 48 without significantly impacting the vacuum packaging system 10'. The packaging, opening and use of the vacuum packaging system 10' of the second preferred embodiment is otherwise similar to the use of the vacuum packaging system 10 of the first preferred embodiment, as will be understood by one having ordinary skill in the art.

It will be appreciated by those skilled in the art that changes could be made to the preferred embodiment of the vacuum package system 10 described above without departing from the broad inventive concept thereof. It is understood, therefore, that this invention is not limited to the particular embodiment disclosed, but is intended to cover modifications within the spirit and scope of the present application.

We claim:

1. A method for packaging a plurality of syringes for transportation in a tray within an evacuated internal cavity of an air impervious flexible film, and the tray including a lip, the method comprising the steps of:
   a) inserting the syringes into the tray by:
      a)(1) inserting a nesting plate into the tray such that a peripheral edge of the nesting plate is positioned on the lip; and
      a)(2) inserting the syringes into cylindrical sleeves in the nesting plate such that a top rim of the sleeves is in contact with a flange of the syringes;
   b) inserting the tray filled with the syringes into the internal cavity;
   c) evacuating the internal cavity to a predetermined vacuum pressure such that the flexible film surrounds and engages the tray and at least portions of the syringes; and
   d) sealing the flexible film such that the predetermined vacuum pressure is generally maintained in the internal cavity.

2. The method of claim 1 further comprising the step prior to step (a) of:

e) grasping one or more of the syringes with a mechanical arm as one of the syringes flows off of a syringe assembly line.

3. The method of claim 1 further comprising the step after step (d) of:
  e) irradiating the sealed flexible film, the tray and the syringes.

4. The method of claim 1 further comprising the steps after step (d) of:
  e) transporting the sealed flexible film and the syringes;
  f) inspecting the flexible film to ensure that the film is engaging the tray and at least portions of the syringes indicating that the predetermined pressure is maintained within the internal cavity;
  g) breaking the flexible film to gain access to the syringes;
  h) removing the tray from the internal cavity; and
  i) removing the syringes from the tray for introduction onto an assembly line for the introduction of medical products into the syringes.

5. The method of claim 1 wherein the syringes are inserted into the tray in step (a) in a series of rows.

6. The method of claim 1 further comprising the steps of:
  e) irradiating the sealed flexible film, the tray and the syringes following step (d); and
  f) introducing an inert purge gas into the evacuated internal cavity prior to step (c) to stabilize and prevent one of changes in chemical composition and discoloration of the syringes in step (e).

7. The method of claim 1 further comprising the steps of:
  e) molding the syringes prior to step (a);
  f) robotically transporting the syringes to an inspection station prior to step (a); and
  g) irradiating the sealed and evacuated internal cavity and the syringes following step (d).

8. The method of claim 1 further comprising the steps of:
  e) transporting the sealed and evacuated flexible film, the tray and the syringes to a filler; and
  f) opening the internal cavity by tearing the flexible film at a tear notch.

9. The method of claim 1 wherein the predetermined vacuum pressure is approximately eight inches of mercury (8 in Hg) such that the flexible film surrounds and engages the tray and at least portions of the syringes in a reduced internal pressure condition and the flexible film generally holds the syringes in the tray without rubbing against each other or otherwise significantly moving during shipping.

10. A method for packaging a plurality of vials each including a head side and a based side for transportation in a tray within an evacuated internal cavity of an air impervious flexible film, the method comprising the steps of:
  a) inserting each of the vials into the tray with their head side proximate a floor of the tray;
  b) inserting the tray filled with the vials and a rigid sheet into the internal cavity;
  c) evacuating the internal cavity to a predetermined vacuum pressure such that the flexible film surrounds and engages at least the rigid sheet and the tray;
  d) sealing the flexible film such that the predetermined vacuum pressure is generally maintained in the internal cavity;
  e) transporting the sealed and evacuated flexible film, the rigid sheet, the tray and the vials to a filler;
  f) opening the internal cavity by tearing the flexible film at a tear notch;
  g) moving the tray, the vials and the rigid sheet out of the flexible film;
  h) inverting the rigid sheet, vials and tray;
  i) placing the rigid sheet, vials and tray on a support surface such that the base sides of the vials are resting on the rigid sheet;
  j) moving the rigid sheet from beneath the base sides such that the base sides are resting on the support surface; and
  k) moving the tray vertically away from the vials.

11. The method of claim 10 further comprising the step prior to step (a) of:
  l) grasping one or more of the vials with a mechanical arm as one of the vials flows off of a vial assembly line.

12. The method of claim 10 further comprising the step after step (d) of:
  l) irradiating the sealed flexible film, the tray and the vials.

13. The method of claim 10 wherein the vials are inserted into the tray in step (a) in a series of rows.

14. The method of claim 10 further comprising the steps of:
  l) irradiating the sealed flexible film, the tray and the vials following step (d); and
  m) introducing an inert purge gas into the evacuated internal cavity prior to step (c) to stabilize and prevent one of changes in chemical composition and discoloration of the vials in step (e).

15. The method of claim 10 further comprising the steps of:
  l) molding the vials prior to step (a);
  m) robotically transporting the vials to an inspection station prior to step (a); and
  n) irradiating the sealed and evacuated internal cavity and the vials following step (d).

16. The method of claim 10 wherein the predetermined vacuum pressure is approximately eight inches of mercury (8 in Hg) such that the flexible film surrounds and engages the tray and at least portions of the vials in a reduced internal pressure condition and the flexible film generally holds the vials in the tray without rubbing against each other or otherwise significantly moving during shipping.

* * * * *